United States Patent [19]

Greene et al.

[11] Patent Number: 4,587,962
[45] Date of Patent: May 13, 1986

[54] TIBIA/ANKLE ORTHOSIS

[75] Inventors: Ted J. Greene, La Canada; Matthew V. Waidelich, Monrovia, both of Calif.

[73] Assignee: United States Manufacturing Company, Pasadena, Calif.

[21] Appl. No.: 578,230

[22] Filed: Feb. 8, 1984

[51] Int. Cl.4 .............................................. A61F 5/00
[52] U.S. Cl. .................................. 128/80 H; 128/88; 128/DIG. 15; 36/2 R
[58] Field of Search ...................... 128/80 H, 88, 80 R, 128/80 C, 87 R, 89, 166, DIG. 15, 80 F; 36/2 A, 2 R, 2 B, 1.5; 2/22, 23, 24

[56] References Cited

U.S. PATENT DOCUMENTS

| | | | |
|---|---|---|---|
| 1,846,642 | 2/1932 | Jensen | 36/2 B |
| 3,955,565 | 5/1976 | Johnson, Jr. | 128/89 R |
| 4,057,056 | 11/1977 | Payton | 128/89 R |
| 4,133,311 | 1/1979 | Karczewski | 128/166 |
| 4,320,748 | 3/1982 | Racette et al. | 128/DIG. 15 |
| 4,378,793 | 4/1983 | Mauldin et al. | 128/80 H |
| 4,494,534 | 1/1985 | Hutson | 128/80 F |
| 4,510,927 | 4/1985 | Peters | 128/80 H |

Primary Examiner—Robert Peshock
Assistant Examiner—John G. Weiss
Attorney, Agent, or Firm—Christie, Parker & Hale

[57] ABSTRACT

A tibia/ankle orthosis includes a flexible jacket shaped to fit around the lower leg of a patient. The jacket has a continuous resilient front section for extending along the front of the tibia and across the width of the tibia. A pair of semi-rigid uprights extend along lateral and medial sides of the jacket. The jacket terminates in lateral and medial flaps that overlap one another at the rear of the patient's lower leg. A footplate is rotatably secured adjacent the lower portion of the jacket for supporting the foot while the jacket is wrapped around the tibia. A narrow slotted opening at the lower front portion of the jacket permits the jacket to be applied from front to rear when wrapping the jacket around the lower leg while the patient's foot is held against rotation when placing the patient's foot on the footplate. The lateral and medial end portions of the jacket overlap uniformly around the patient's calf. A first set of straps on one flap extend through the opposite side of the jacket, and are wrapped in a first direction around the jacket and tightened to apply torque in a first direction of rotation. A second set of straps on the other flap extend in an opposite direction around the jacket and are tightened to apply torque in an opposite direction. This permits tightening of the jacket around the lower leg with torque applied in opposite directions to ensure good support while uniformly distributing the pressure around the leg, ensuring uniform fit and comfort of the orthosis.

15 Claims, 4 Drawing Figures

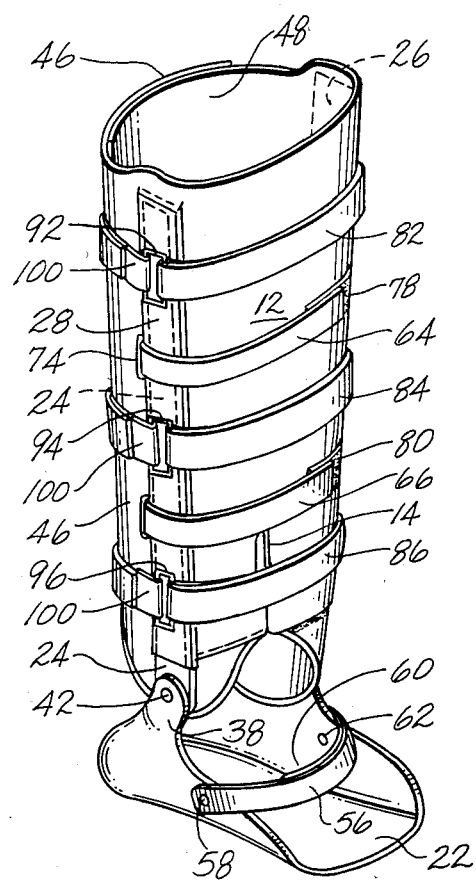

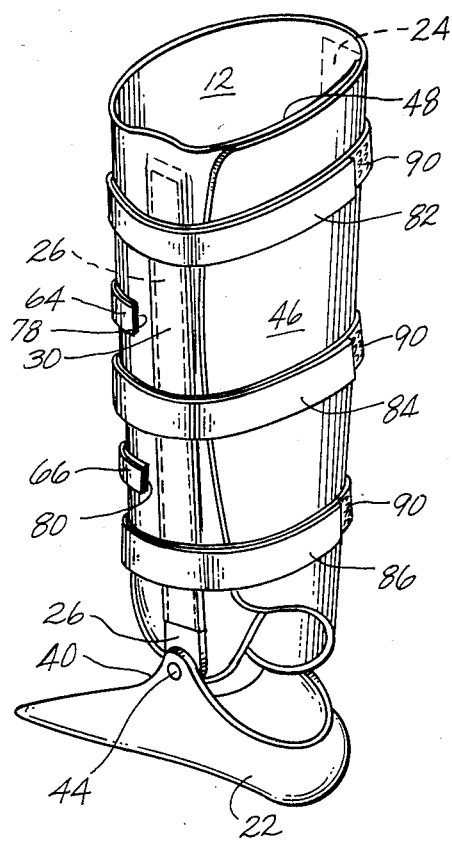

TIBIA/ANKLE ORTHOSIS

FIELD OF THE INVENTION

This invention relates in general to orthoses, and more particularly to an orthosis that permits limited ambulation of a patient during treatment of injuries such as fractures of the tibia or ankle sprains.

BACKGROUND OF THE INVENTION

Within the past few years special types of light weight fracture braces have been used for the treatment of tibia fractures after the initial period of treatment in a cast of plaster of paris. The cast is used initially to immobilize the fracture. The plaster cast is uncomfortable because it is heavy and is not removable during its long period of use. It also limits the mobility of the patient. After the plaster cast is removed the special light weight fracture braces can be worn to increase patient mobility while providing the support necessary to prevent twisting, or other undue stress on the tibia during the healing process. These fracture braces are light in weight because they are commonly made of plastic; and they are usually designed to be removed, adjusted, and reused on the patient. Some of these light weight fracture braces include a foot plate attached to the bottom of a tibia brace in the form of a jacket or the like that wraps around the tibia. The foot plate is secured to the tibia supporting jacket through flexion joints that permit limited rotational motion of the ankle. This brace allow the patient a limited amount of mobility while the brace is worn. Thus, the light weight fracture braces provide a substantial benefit to the patient during the healing process when compared with a plaster cast.

Problems have been experienced with prior light weight fracture braces. The supporting jackets of these braces are commonly applied from rear to front of the patient's leg. This allows the patient's foot to be held in a normal position while the jacket is being placed on the patient's leg. On the other hand, if the jacket is applied from front to rear, the prior braces require too much movement of the patient's foot. It is best if the patient's foot is not moved from its normal position when the brace is applied. The braces applied from rear to front use the fatty tissue of the calf in the back of the tibia for attaching the brace to the leg. The jacket has an opening at the front so that the main portion of the jacket can be wrapped around the calf, often while the front opening is adjusted at the front of the tibia. It is difficult to make a brace that conforms well to the size and shape of the fatty tissue of the calf for all patients while ensuring that the size of the jacket is easily adjusted at the front of the tibia. In many cases the point of adjustment in front of the tibia applies undue pressure to the bony prominence along the front of the patient's tibia. Tibia supporting jackets made of hard plastic also are especially uncomfortable when tightened against the bony front portion of the patient's tibia. Another problem is that many of these prior art fracture braces are not always comfortable when the tibia supporting jacket is tightened. They are not designed to ensure that torque is uniformly applied to the patient's leg when the straps on the tibia supporting jacket are wrapped around the jacket and tightened. The tibia supporting jacket is often crumpled or too bulky when tightened. In either case the brace can be highly uncomfortable for the patent.

This invention provides an orthosis that overcomes the problems associated with the prior art light weight fracture braces. The tibia supporting jacket of the orthosis can be applied from front to rear of the patient's tibia. The adjustment is in the rear of the jacket, along the fatty tissue of the patient's calf. The front of the jacket thus can provide continuous padding along the bony prominence along the front of the patient's tibia, while the adjustment at the rear of the jacket along the patient's calf is much more comfortable than the prior art braces in which the jacket is applied from rear to front. The orthosis also can be applied from front to rear while leaving the patient's foot in the normal position. In addition, the tibia supporting jacket can be applied and tightened without torquing the patient's leg one way or the other. The jacket is held in a neutral position around the tibia when tightened to its fullest extent, and the jacket also folds together and is tightened in such a way the the material does not crumple or become bulky. The result is an orthosis which is comfortable to wear while still providing the required amount of support. In addition to providing the support necessary for fractures of the tibia, the orthosis also can be used as a means of support for ankle sprains.

SUMMARY OF THE INVENTION

Briefly, the invention comprises an orthosis having a flexible jacket for extending around and conforming to the shape of the patient's leg from about the ankle to about the knee. In one embodiment, a foot plate pivotally attached to the jacket permits rotation of the foot plate about a generally horizontal axis extending through the medial and lateral sides of the patient's leg. The front of the jacket has continuous padding for extending along the bony prominence along the front of the patient's tibia. The jacket also has padding extending away from opposite sides of the jacket front to form a foldable means for encasing the leg. The foldable side portions of the jacket form an opening in the rear of the jacket adjacent to the patient's calf. The jacket can be placed around the patient's leg from front to rear, with straps or the like on the jacket being tensioned to tighten the jacket around the patient's leg and retain an adjustable amount of circumferential pressure on the patient's leg. The lower front portion of the jacket opens to allow the jacket front to be fitted over the front of the tibia with the patient's foot inserted into the foot plate while the foot remains held in a normal position.

In another embodiment, the foldable side portions of the jacket are formed by a pair of flaps that fold one over the other along the rear of the patient's calf. One flap has flexible strap-like tighteners for being wrapped in one direction around the jacket for securing one flap around the patient's leg, while the other flap has strap-like tighteners for being wrapped in an opposite direction around the jacket for securing the other flap around the patient's leg. The foldable flaps allow the jacket to be wrapped firmly around the patient's leg without bunching or crumpling the jacket material. The straps on one flap are tightened so the jacket applies torque to the patient's leg in one rotational direction, while the straps on the other flap are tightened so the jacket applies torque to the patient's leg in an opposite direction. This leaves the jacket in a straight neutral position around the patient's leg while the jacket applies circumferential pressure to immobilize the tibia. The result is a jacket which is comfortable because of its ability to fit evenly around the patients leg and to distribute torque loading uniformly around the patient's leg.

These and other aspects of the invention will be more fully understood by referring to the following detailed description and the accompanying drawings.

DRAWINGS

FIG. 3 is a front perspective view showing the orthosis in a closed position during use.

FIG. 4 is a rear perspective view showing the orthosis in a closed position during use.

DETAILED DESCRIPTION

Figure 1:
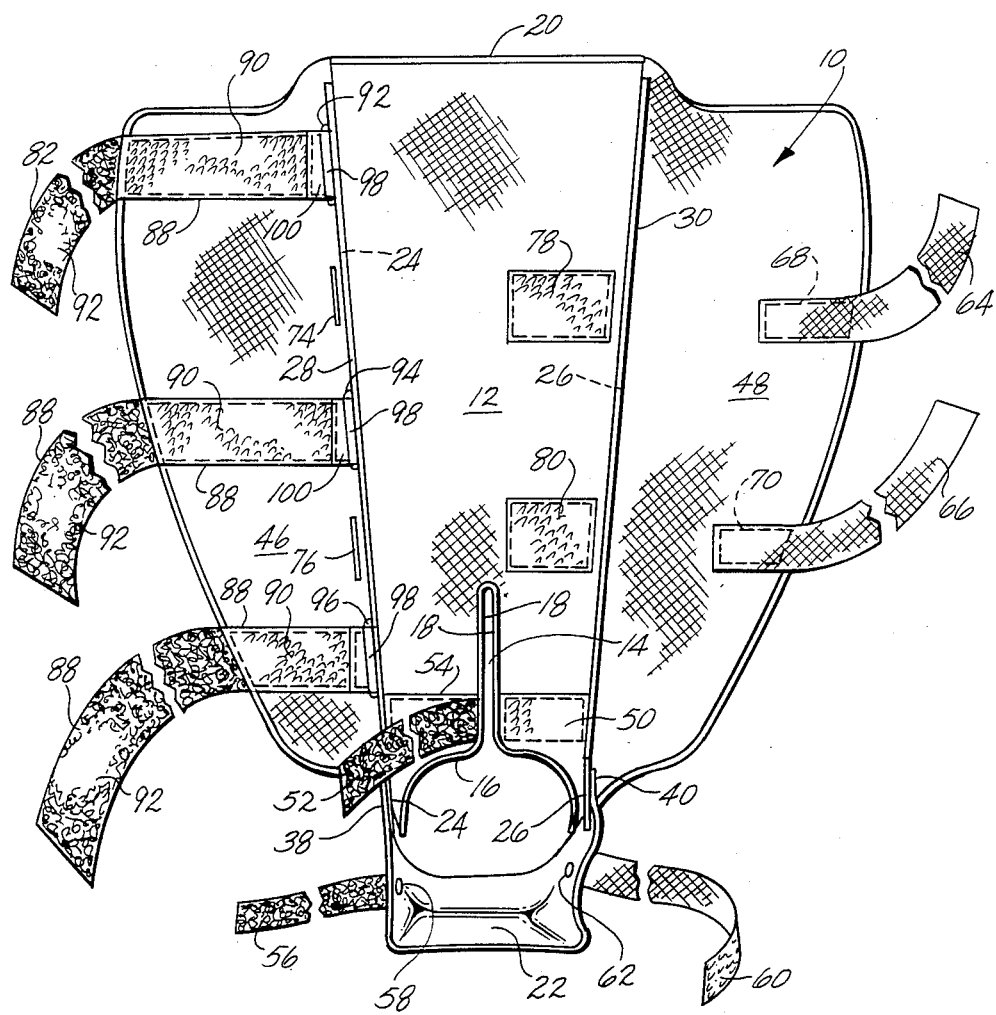
FIG. 1 is a fragmentary front elevation view showing an orthosis according to principles of this invention opened outwardly into a flat form to show the exterior of the orthosis.
Figure 2:
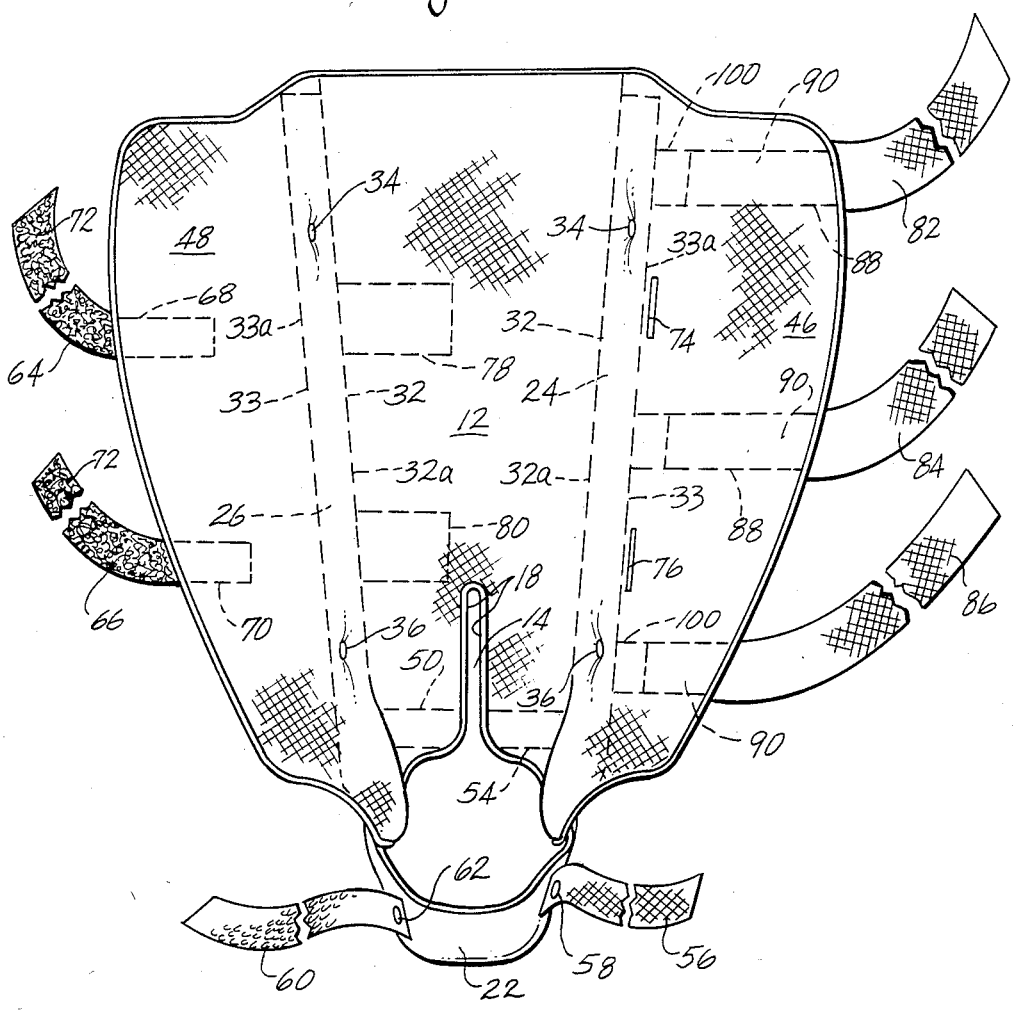
FIG. 2 is a fragmentary rear elevation view showing the orthosis opened outwardly and flat form to show the inside of the orthosis.

FIG. 1 shows an improved orthosis, according to principles of this invention, as viewed in front elevation. FIG. 2 is a rear elevation view of the orthosis. In both of these views a jacket portion of the orthosis is shown in its maximum open position folded outwardly to more clearly show all components of the orthosis. FIG. 1 shows the exterior of the orthosis and FIG. 2 shows the interior of the orthosis. FIGS. 3 and 4 are front and rear perspective views, respectively, showing the jacket portion of the orthosis in a closed position in which the orthosis is wrapped around the leg of a patient (not shown) during use.

Referring to FIGS. 1 and 2, the orthosis includes a jacket 10 made of soft flexible padding adapted to be wrapped around the lower leg of a patient. The jacket is of such shape and size to extend upwardly from the vicinity of the ankle to the vicinity of the knee so as to encapsulate and conform to the anatomical configuration of the lower leg. In the illustrated embodiment, the flexible padding which forms the jacket is a single piece of padding having an interior layer of a resilient flexible plastic foam material inside inner and outer protective layers of a flexible fabric. The inner and outer layers of fabric are stitched together around the entire periphery of the jacket to contain the interior layer of resilient plastic foam. Preferably, the interior layer is an open cell foam material and the inner and outer layers of fabric are materials capable of "breathing" well. By "breathing" is meant that each material, the flexible fabric and the open cell foam, is porous to air and water and is capable of absorbing fluids at least in moderate amounts. The preferred materials are an interior layer of open cell polyurethane foam and the outer and inner layers of fabric are preferably velour.

The layer of padding which forms the jacket includes an elongated front section 12 which preferably comprises a single intregral piece that extends lengthwise from just above the ankle to just below the knee. The front section 12 of the jacket is sufficiently wide to overlie approximately the front half of the patient's leg. The front section of the jacket is generally rectangular in shape, although it tapers wider from a lower edge 16 upwardly toward an upper edge 20 of the jacket. When the front section 12 of the jacket is in use overlying the front of the patient's leg, the flexible piece of padding is continuous along the bony prominence along the front of the tibia. In other words, the padding provided by the front section 12 of the jacket is entirely flexible and resilient continuously along the front of the tibia. The jacket does not have a rigid shell or the like in contact with the bony prominence along the front of the patient's tibia, nor is the jacket adapted for opening with a seam or other door closure or the like extending along the front center of the patient's tibia. The jacket is entirely flexible and resilient in its contact with the tibia which enhances the comfort of the orthosis.

A narrow slotted opening 14 extends upwardly a short distance along the bottom center of the front section 12 of the jacket. In the illustrated embodiment, the slotted opening extends about one-fourth the length of the entire front section 12. The slotted opening opens through the lower edge 16 of the jacket front. This portion of the jacket is inverted U-shaped and extends over the lower front portion of the patient's leg near the front of the ankle joint. The narrow slot provides a means for opening the lower portion of the jacket front when fiting the jacket from front to rear on the patient's lower leg, as will become more easily understood from the description of follow. The narrow slot 14 is bounded on opposite sides by two confronting straight edges 18 that retain the resilience and flexibility of the padding at the front of the jacket. No fastening means or the like that would add rigidity along the slot are used.

A footplate 22 is connected to the jacket to hold the footplate below the jacket spaced a short distance below the curved lower edge 16 of the jacket. The footplate connects to the jacket through lateral and medial uprights 24 and 26, respectively, secured to the jacket along opposite sides of the front section 12 of the jacket. The uprights overlie the outer face of the jacket, and separate elongated pieces 28 and 30 of a sturdy flexible fabric such as canvas overlie the lateral and medial uprights. Stitching 32 around the perimeter of each piece secures the pieces to the jacket so that the length of each upright is encased within a corresponding flexible piece. Upper and lower rivets 34 and 36 extend through each flexible piece to rigidly affix each upright to the jacket. The uprights diverge slightly upwardly, as shown best in FIG. 1, forming lateral and medial boundries along opposite sides of the front section 12 of the jacket. The lateral and medial uprights are preferably made of plastic and are reasonably stiff, but each is capable of bending axially as well as twisting somewhat. The stiffness of each upright is sufficient to provide reasonably good resistance to bending of the leg axially and twisting of the leg about its axis when the orthosis is used.

The lower portion of each upright is exposed adjacent the outer face of the jacket, and the opposite lateral and medial sides of the footplate have upwardly extending lateral and medial projections 38 and 40 that overlie the lower exposed portions of the uprights. Each upright attaches to the footplate throught a pivot. The lateral projection 38 of the footplate overlies the exposed lower portion of the lateral upright 24, and a lateral piviot pin 42 (shown in FIG. 3) fastens the footplate to the lateral upright. Similarly, the medial projection 40 of the footplate overlies the exposed lower portion of the medial upright 26, and a medial pivot pin 44 (shown in FIG. 4) pivots the footplate to the medial upright. The lateral and medial pivot pins are aligned along a generally horizontal pivot axis extending from the medial side of the patient's leg to the lateral side generally through the axis of rotation of the ankle joint. When the patient's foot is in the footplate and the jacket is secured to the patient's lower leg, the pivotal attachment of the footplate to the jacket permits normal forward and back rotation of the foot about the ankle joint, while the attachment of the footplate to the jacket provides resistance to angular rotation of the foot in the left or right directions relative to the lower leg. The orthosis also resists twisting of the lower leg relative to the fixed position of the patient's foot.

The jacket also includes lateral and medial flaps 46 and 48, respectively, extending from the lateral and medial uprights in a direction away from the front section 12 of the jacket. Each flap is formed by marginal end portions of the same flexible resilient padding from which the front section 12 of the jacket is formed. Both flaps are approximately the same size and shape, each tappering generally wider toward the top of the jacket.

The lateral and medial uprights are normally constrained by their attachment to the footplate so as to extend uprightly in separate planes each extending generally perpendicularly to the plane of the front section 12 of the jacket. The rows of stitching 32 adjacent the front edges of the lateral and medial uprights form natural fold lines 32a about which the side portions of the jacket, to which the lateral and medial uprights are attached, are normally foldable at right angles away from the front section 12 of the jacket. The rows of stitching 33 adjacent the rear edges of the lateral and medial uprights form natural fold lines 33a about which the lateral and medial flaps 46 and 48 are foldable through an angle relative to the adjacent portions of the jacket to which the uprights are secured. The lateral and medial flaps are each able to fold to a position generally parallel to and spaced to the rear of the front section 12 of the jacket so that the lateral and medial flaps can be folded one over the other to form a closed jacket that conforms generally to the anatomical configuration of the lower leg. Although either flap could be designed to overlap the other flap in use, in the illustrated embodiment the medial flap is designed to be folded to the inside of the closed jacket, with the lateral flap then folded over the outer face of the medial flap to form the outer rear face of the closed jacket. The orthosis is thus formed as a continuous resilient piece of flexible padding for extending across the front of the patient's leg between the more rigid lateral and medial uprights, with separate flexible resilient padding formed as foldable flaps extending away from the uprights and adapted to fold one over the other to extend across the rear of the lower leg.

The orthosis is used by applying it from front to rear of the patient's lower leg. The slotted opening 14 in the lower front portion of the jacket front section 12 allows the portions of the jacket adjacent the slot to be folded back to form a large open area at the lower front of the jacket so the patient's foot can be slipped forward from rear to front over the footplate and then under the folded back open region at the bottom of the jacket front section. In this way, the patient's foot can be held in a normal position while placing it over the footplate, after which the patients foot can be lowered to rest on the footplate. The lower front section of the jacket is then closed and the patient's foot is secured to the footplate. Once the patient's foot is in position supported on the footplate, with the front section 12 of the jacket overlying the front portion of the patient's leg, the narrow slotted opening 14 at the front of the jacket is held closed preferably by a thistle cloth or hook and pile fastener such as the type sold under the trademark "Velcro." In the illustrated embodiment a short section 50 of a hook fastener is secured to the front face of the jacket front section 12 adjacent one edge 18 of the slotted opening 14. On the opposite side of the slotted opening a flexible strap 52 having a pile fastener on its inside face is fastened to the front face of the jacket by stitching 54. The flexible strap type fastener 52 thus can be pulled across the lower portion of the slotted opening 14 and affixed to the fastener 50 to hold the lower portion of the jacket front section 12 in a closed position against the lower front portion of the patient's leg. Flexible thistle cloth fasteners also are secured to lateral and medial sides of the footplate for securing the patient's foot in the footplate. These fasteners include a flexible strap 56 with a pile fastener on its inside face affixed to the lateral side of the footplate by a rivet 58, and a flexible strap 60 having a hook fastener on its outer face secured to the medial side wall of the footplate by a rivet 62.

The jacket is secured to the patient's lower leg by folding the medial flap 48 around the rear half of the patient's leg (over the patient's calf). The medial flap is then tightened around the patient's leg by a pair of upper and lower flexible medial straps 64 and 66 secured to the medial flap by stitching 68 and 70, respectively. The upper and lower medial straps are fixed to the medial flap at elevations corresponding to about one-third and two-thirds of the height of the flap. Each medial strap is a relatively short strap secured to the medial flap adjacent its outer edge, with free ends of each strap extending away from the outer edge of the flap. The free end of each medial strap has a thistle cloth pile fastener 72 on its inside face. A pair of vertically spaced apart upper and lower medial strap receiving slots 74 and 76 extend through the lateral flap 46 immediately adjacent the lateral upright 24. The two slots are at elevations corresponding to the elevations of the upper and lower medial straps 64 and 66. The two slots are also axially aligned on a common axis parallel to the adjacent lateral upright 24. Upper and lower hook fasteners 78 and 80 are formed as short fixed sections of fastener material on the front face of the front section 12 of the jacket. The upper fastener 78 is affixed to the front of the jacket adjacent the medial flap 48 and is located in a line between the upper strap fastener 64 and the slot 74. Similarly, the lower fixed fastener section 80 is affixed adjacent the medial flap 48 on a line between the lower strap fastener 66 and the lower slot 76.

After the medial flap 48 is folded over the rear of the patient's leg, the medial straps 64 and 66 are threaded through the upper and lower slots 74 and 76, respectively, and the straps are tensioned to torque the jacket in one direction of rotation around the patient's leg. The width of the medial flap is such that it normally folds over about one half of the patient's calf to allow room for moving the flap toward the opposite side of the jacket without bunching the material when the medial straps are tightened. The medial straps are pulled around to the front of the jacket and the Velcro fasteners on the straps are secured to the upper and lower Velcro fasteners 78 and 80 on the front of the jacket. The fasteners 64 and 66 maintain the tension on the straps to hold the jacket in its torqued position. The fastened positions of the medial straps are shown best in FIG. 3.

The lateral flap 46 is then folded over the fastened medial flap. The lateral flap easily fits over the medial flap without bunching the material. This is best illustrated in FIGS. 3 and 4. Long upper, intermediate and lower flexible straps 82, 84, and 86, respectively, are secured to the lateral flap. These straps are each attached to the front face of the lateral flap by stitching 88, and free ends of each strap extend a substantial distance laterally away from the outer edge of the flap. The affixed portions of the straps extend across the entire width of the lateral flap, and these portions of the straps have Velcro hook fasteners 90 on them. Velcro pile fasteners 92 are affixed to free end portions of the lateral straps. Upper, intermediate, and lower fastener rings 94, 96, and 98, respectively, are affixed to the outer face of the lateral flap at the juncture between each Velcro fastener section 90 and the lateral upright 24. Each fastener ring has a corresponding narrow elongated tubular rotatable friction-reducing roller 98. Each ring and its accompanying roller is affixed to the jacket by a short length of fabric such as canvas which is folded back on itself and secured to the jacket to form a short flexible loop 100 for holding the fastener rings.

After the medial flap has been folded over the rear of the patient's leg and torque applied to the medial flap, and after the lateral flap is folded over the medial flap, torque is then applied to the lateral flap in a direction opposite to the direction of the torque applied to the medial flap. The reverse torque is applied to the lateral flap by wrapping each of the long straps 82, 84, and 86 around the front of the jacket in a direction opposite to the direction that each of the short medial straps 64 and 66 extends around the front of the jacket. Each of the long lateral straps is then threaded through a corresponding one of the fastener rings 92, 94, and 96, and each lateral strap is then pulled tightly through the ring using the rotation of the rollers to assist in tightening the straps to apply the reverse torque. The straps are then each folded back on themselves, and the Velcro pile fastener section 92 of each strap is attached to a corresponding Velcro hook fastener section 90 at the rear of the jacket, as shown best in FIG. 4, to retain the torque applied by the straps. The opposite rear portions of the jacket are thus tensioned to apply bi-directional torque around the lower leg and maintain it as uniformly distributed circumferential pressure around the leg.

Thus, the present invention provides a sturdy yet light-weight and comfortable orthosis used on the patient's lower leg for treating fractures of the tibia, ankle sprains, or any other below knee injury. The orthosis permits the normal front and backward rotation of the ankle joint so the orthosis can be used as a walking cast in which the ankle is allowed to be movable after an initial plaster cast is removed. The orthosis, when applied, however, provides good support to resist lateral bending or twisting of the lower leg. The narrow slotted opening of the base of the jacket front permits the orthosis to be applied from front to rear while the foot is held in a normal position without moving the foot. This allows the fatty tissue of the calf in the back of the leg to be used for taking most of the pressure when attaching the jacket tightly to the lower leg. The front of the jacket comprises continuous resilient padding across the front of the lower leg and along the front of the tibia bone, which can otherwise be uncomfortable if contacted directly by a hard plastic jacket or shell, fasteners, or other rigid or simi-rigid closures or the like. The jacket of the orthosis also can be wrapped around the patient's lower leg and overlapped at the rear of the leg, and each end portion of the jacket at the rear of the leg then can be torqued in opposite directions when wrapping the jacket tightly around the leg. This allows the jacket to fold smoothly around the patient's lower leg without crumpling the material, or otherwise making it bulky, or uncomfortable. The jacket is left in a straight neutral position after the jacket is torqued in opposite directions by the first set of small straps and the second set of main straps. Thus, the tibia is not torqued to the left or the right and is also more comfortable because the wrapping of the jacket around the tibia is uniform.

What is claimed is:

1. A tibia/ankle orthosis comprising a flexible jacket shaped to fit around the lower leg of a patient, the jacket having a continuous front section for extending along the front of the tibia and across the width of the tibia, a pair of more rigid uprights on opposite sides of the front section for extending along lateral and medial sides of the tibia, the jacket terminating in lateral and medial flaps that overlap one another at the rear of the tibia, a footplate rotatably secured to lower portions of the uprights for supporting the foot while the jacket is wrapped around the tibia, a narrow upright slotted opening extending along the lower portion of the jacket front section immediately above the footplate for being opened to permit the patient's foot to be placed on the footplate without significant front-to-rear rotation of the foot about the ankle joint while placing the jacket around the tibia from front to rear, and means carried on the jacket for tightly wrapping the jacket around the tibia after the foot is supported on the footplate.

2. Apparatus according to claim 1 including fastening means for wrapping around the lower portion of the jacket to maintain the slotted opening in a closed position.

3. Apparatus according to claim 1 in which the narrow slotted opening extends for only a short portion of the height of the front section of the jacket and is bounded by flexible marginal edges.

4. A tibia/ankle orthosis comprising a flexible jacket shaped to fit around the lower leg of a patient, the jacket having a front section for extending along the tibia and across the width of the tibia, the jacket terminating in lateral and medial flaps that overlap one another at the rear of the tibia when the jacket is wrapped around the tibia, one or more first straps on one flap for extending through the opposite side of the jacket so the first straps can be wrapped around the front of the jacket and tensioned to pull on their corresponding flap to apply torque in one rotational direction around the jacket, and one or more second straps on the other flap for extending around the front of the jacket in a direction opposite to the direction in which the first straps are wrapped so that tensioning of the seconds straps pulls on their corresponding flap to apply torque in a rotational direction opposite to that produced by tensioning of the first straps, so that the jacket can be tightly wrapped around the tibia with the first and second tensioned straps applying bi-directional torque around the tibia.

5. Apparatus according to claim 4 including fastening means on the jacket for holding the tensioned first and second straps in fixed positions to maintain the torqued positions of the straps.

6. Apparatus according to claim 4 including a footplate rotatably secured to a lower portion of the jacket for supporting the foot while the jacket is wrapped around the tibia.

7. Apparatus according to claim 6 including means for pivoting the footplate to the jacket so the foot can rotate forward or backward about the ankle joint.

8. Apparatus according to claim 7 including lateral and medial uprights having a rigidity greater than that of the jacket for extending along opposite sides of the jacket to provide resistance to bending of the tibia laterally or medially and to cooperate with the footplate and the jacket to resist rotation of the tibia relative to the foot.

9. A tibia/ankle orthosis comprising:
a flexible jacket shaped to fit around the lower leg of a patient, the jacket having a front section for extending along the tibia and across the width of the tibia, the jacket terminating in lateral and medial flaps that overlap one another at the rear of the tibia when the jacket is wrapped around the tibia;
a pair of uprights secured to the jacket for extending along lateral and medial sides of the tibia;
foot support means rotatably secured to lower portions of the uprights for supporting the foot while the jacket is wrapped around the tibia; and
one or more first straps on one flap for extending through the opposite side of the jacket so the first straps can be wrapped around the jacket and tensioned to pull on their corresponding flap to apply torque in one rotational direction around the jacket, and one or more second straps on the other flap for extending around the jacket in the direction opposite to the direction in which the first straps are wrapped so that tensioning of the second straps pulls on their corresponding flap to apply torque in a rotational direction opposite to that produced by tensioning of the first straps, so that the jacket can be tightly wrapped around the tibia with the first and second tensioned straps applying bi-directional torque around the tibia.

10. Apparatus according to claim 9 including fastening means on the jacket for holding the tensioned first and second straps in fixed positions to maintain the torque positions of the straps.

11. Apparatus according to claim 9 in which the lateral and medial uprights have a rigidity greater than that of the jacket for extending along opposite the sides of the jacket to provide resistance to bending of the tibia laterally or medially and to cooperate with the foot support means and the jacket to resist rotation of the tibia relative to the foot.

12. Apparatus according to claim 9 including a narrow upright slotted opening extending along the lower portion of the jacket front section immediately above the foot plate for being opened to permit the patient's foot to be placed on the foot support means without significant front-to-rear rotation of the foot about the ankle joint while placing the jacket around the tibia from front-to-rear.

13. Apparatus according to claim 12 including fastening means for wrapping around the lower portion of the jacket to maintain the slotted opening in a closed position.

14. Apparatus according to claim 12 in which the narrow slotted opening extends for only a short portion of the height of the front section of the jacket and is bounded by flexible marginal edges.

15. Apparatus according to claim 9 in which the uprights are more rigid than the jacket and overlie lateral and medial sides of the patient's leg when the jacket is wrapped around the lower leg, and in which the first straps extend through corresponding slotted openings in the jacket behind the upright on the opposite side of the jacket.

* * * * *